United States Patent
Szabo et al.

[11] 3,940,386
[45] Feb. 24, 1976

[54] SUBSTITUTED CINNAMOYL-PIPERAZINE-PYRIDYL COMPOUND

[75] Inventors: Suzanne Szabo, La Tour de Peilz; Francois Molnar, Blonay, both of Switzerland; Roland-Yves Mauvernay, Riom, France; Chau Levan, Monthey, Switzerland; Peter Radanov Statkov, Geneva, Switzerland; Danielle Straumann, Martigny, Switzerland; Olga Lerik Milovanovic, Bex, Switzerland

[73] Assignee: Cermol S.A.

[22] Filed: June 21, 1974

[21] Appl. No.: 481,794

[30] Foreign Application Priority Data
June 29, 1973 Switzerland.......................... 9528/73
May 20, 1974 Switzerland.......................... 6899/74

[52] U.S. Cl.............................. 260/240 K; 424/250
[51] Int. Cl.². ............... C07D 401/06; C07D 401/12
[58] Field of Search...................... 240/240 D, 240 K

[56] References Cited
UNITED STATES PATENTS

| | | | |
|---|---|---|---|
| 2,766,233 | 10/1956 | Kartinos et al. ................. | 260/240 F |
| 2,882,271 | 4/1959 | Janssen .................... | 260/240 K UX |
| 3,511,841 | 5/1970 | Archer....................... | 260/240 K X |
| 3,573,291 | 3/1971 | Fauran et al.................... | 260/240 K |
| 3,773,939 | 11/1973 | Janssen ....................... | 260/240 K X |

FOREIGN PATENTS OR APPLICATIONS

| | | | |
|---|---|---|---|
| 601,119 | 7/1960 | Canada........................... | 260/240 D |
| 29,508 | 9/1970 | Japan.............................. | 260/240 K |

*Primary Examiner*—Allen B. Curtis
*Attorney, Agent, or Firm*—Stevens, Davis, Miller & Mosher

[57] ABSTRACT

Compounds of the formula:

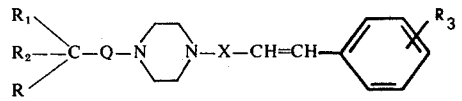

wherein
X represents a carbonyl group C=O or a methylene group —CH₂—,
R represents a phenyl, mono- or di-halophenyl or 2-pyridyl group,
$R_1$ represents a pyridyl or $C_{3-7}$-cycloalkyl group,
$R_2$ represents hydrogen, hydroxy or a $C_{1-5}$-alkyl group,
$R_3$ represents 1 to 3 groups which can be hydrogen, halogen, $C_{1-3}$-alkyl, methoxy or dioxymethylene,
Q represents the $(CH_2)_n$ group, $n$ having the value 0, 1, 2, 3, the —CH=CH—CH₂— or —O—CH₂—CH₂— group,
have analgesic, hypothermic and anti-depressant properties, accompanied by a weak psycholeptic action, anticonvulsive and slightly sedative properties, vasodilatory, spasmolytic, anti-bronchiospastic, anti-histaminic, anti-allergical, anti-emetical properties, and which increase the cerebral and myocardic bloodrate and -oxygenation.

2 Claims, No Drawings

SUBSTITUTED CINNAMOYL-PIPERAZINE-PYRIDYL COMPOUND

This invention concerns piperazines having the general formula:

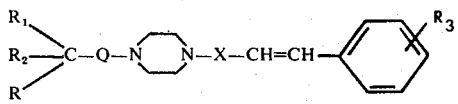   I wherein
X represents a carbonyl group >C=O or a methylene group —$CH_2$—,
R represents a phenyl, mono- or di-halophenyl or 2-pyridyl group,
$R_1$ represents a pyridyl or $C_{3-7}$-cycloalkyl group,
$R_2$ represents hydrogen, a hydroxy or a $C_{1-5}$-alkyl group,
$R_3$ represents 1 to 3 groups which may be hydrogen, halogen, $C_{1-3}$-alkyl, methoxy or dioxy methylene,
Q represents a —$(CH_2)_n$— group, $n$ having the value 0, 1, 2, 3, the —CH=CH—$CH_2$— group or the —O—$CH_2$—$CH_2$-group.

These novel compounds can be prepared by reacting a compound

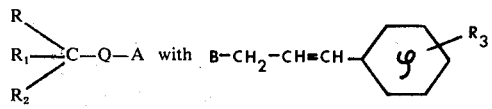

wherein one of A and B represents a chlorine or bromine atom or a tosyl residue, and the other a piperazinyl group. In the particular case where $R_2$ is a $C_{1-5}$-alkyl group, the compound $R_2$ = Li can be reacted with a halide of $C_{1-5}$-alkyl. When Q represents the $(CH_2)_n$ group, $n=2$ or 3, the —CH=CH-$CH_2$— group or —O—$CH_2$—$CH_2$— group, the novel compounds can also be obtained by reacting the:

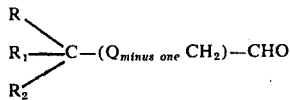

molecule with a corresponding piperazinyl compound in the presence of formic acid.

The following may be reacted: either:
1. the R,$R_1$-disubstituted methyl chloride with
   a. the cinnamoyl piperazine to obtain the 1-(R,$R_1$)-methyl-4-cinnamoyl piperazine (X = >C=O), or
   b. the cinnamyl piperazine to obtain the 1-(R,$R_1$)-methyl-4-cinnamyl piperazine (X = —$CH_2$—) or:
2. the 1-(R,$R_1$)-methyl piperazine with
   a. cinnamyl chloride to obtain the 1-(R,$R_1$)-methyl-4-cinnamyl piperazine (X = —$CH_2$—) or cinnamoyl chloride to obtain the 1-(R,$R_1$)-methyl-4-cinnamoyl piperazine (X = >C=O).

One method of carrying out the process according to (1) (a), (b) or (2) (a) respectively consists in reacting, by refluxing R,$R_1$-disubstituted methyl chloride with 1-cinnamoyl- or 1-cinnamylpiperazine respectively, or cinnamyl chloride with 1-R,$R_1$-methyl piperazine, in substantially equimolar proportions, in the presence of an alkaline carbonate, in removing the mineral salts, adding ethyl acetate and acidifying with hydrochloric acid, which provides the corresponding product in the form of its crystallized hydrochloride.

According to the invention, the alkaline carbonate used is acidic sodium carbonate.

Said acidification is effected with hydrochloric acid, preferably with an organic solvent saturated with HCl, said organic solvent being desirably isopropanol.

Another particular method of carrying out the process according to (1) (a), (b) or (2) (a), respectively, consists in reacting the above-mentioned compounds in N,N-dimethylformamide by heating the mixture to 40°–50°C in the presence of an alkaline carbonate.

According to the invention, the alkaline carbonate used is preferably neutral potassium carbonate.

The above procedure is then followed.

Another particular method for carrying out the process consists in slowly adding cinnamoyl chloride to a cooled organic solution of 1-(R,$R_1$)-methyl piperazine in substantially equimolar proportions, stirring at room temperature and then heating at 40°–50°C for several hours, removing the mineral salts after cooling, and acidifying with hydrochloric acid, which provides the corresponding product in the form of a crystallized hydrochloride.

According to the invention, the alkaline carbonate used is preferably anhydrous neutral sodium carbonate.

Said acidification is effected with hydrochloric acid, preferably with an HCl saturated organic solvent, said organic solvent preferably being isopropanol.

According to a particularly desirable method of carrying out the process according to the invention, the compounds to be reacted are in solution in an appropriate amount of organic solvent, for instance dry benzene.

Before adding the organic solution of cinnamoyl chloride, the solution of the starting substituted piperazine is cooled to a temperature below room temperature, preferably to about 5°C.

Preferably, the organic solution of cinnamoyl chloride is added dropwise, so that the temperature of the mixture is always maintained at 10°C at the most.

According to another aspect, the invention also concerns a process for obtaining 1-(R,$R_1$)-methyl-4-cinnamyl piperazine, according to which 1(R,$R_1$)-methyl-4-cinnamoyl piperazine obtained according to the invention is reduced, by boiling with lithium aluminium hydride, $LiAlH_4$ in an ether solution, then the reaction is conducted under reflux to completion, the mixture is cooled to approximately −10°C, and the complex formed is decomposed at a temperature of −5° to −10°C, then it is filtered, the aqueous layer is extracted with ether, the ether phase is dried with $Na_2SO_4$, acidified with hydrochloric acid and the product is obtained in the form of crystallized di-hydrochloride.

The ether used for extracting the aqueous layer in the above process is preferably isopropyl ether.

The above acidification is effected with hydrochloric acid, preferably an organic solvent saturated with HCl, said organic solvent preferably being ethanol.

According to the invention we have found, surprisingly, that pharmaceutical compositions containing the novel compounds described, wherein X is the group >C=O, exhibit, at therapeutical doses, analgesic, hypothermic and anti-depressant activities accompanied by a weak psycholeptic action.

We have also found that pharmaceutical compositions containing the novel compounds according to the invention, wherein X is the group —$CH_2$—, exhibit at therapeutical doses, myorelaxant properties with respect to smooth muscles (vessels, bronchii, intestines). These products also inhibit the spasm of smooth muscles caused by various spasmogenous substances.

EXAMPLE 1

21.6 g (0.1 mole) of 1-cinnamoyl piperazine (melting point: 80°–81°C), 8 g of $NaHCO_3$ and 16.7 g (0.1 mole) of cyclopropylphenyl methyl chloride (boiling at 122°–123°C, 100 mm of mercury) in 70 ml of n-butanol were refluxed for 18 hours. After cooling, the mineral salts were filtered off, to the mother liquors 100 ml of ethyl acetate were added and the clear yellow solution formed was acidified with a solution of isopropanol saturated with HCl. The 1-(cyclopropyl phenyl)-methyl-4-cinnamoyl piperazine hydrochloride crystallized out. After a few hours, it was filtered, washed and dried. 33.9 g of crude product were obtained, which had a melting point of 216°–222°C (dec).

After recrystallization in methanol, a colorless crystalline powder was obtained, melting between 230° and 235°C (dec). The overall yield was 79%.

EXAMPLE 2

To a solution of 0.58 g of $LiAlH_4$ in 40 ml of absolute ether was added a solution of 5.2 g (0.015 mole) of 1-(cyclopropyl)-phenyl-methyl-4-cinnamoyl piperazine in 60 ml of absolute ether, so as to keep the mixture constantly boiling. When the addition was complete, the mixture was kept for another 24 hours at reflux. Then it was cooled to −10°C, and the complex was decomposed, between −5° and −10°C, with 10 ml of water.

Then it was filtered on fullers earth, the two layers were separated, the aqueous layer extracted three times with 50 ml of isopropyl ether and the collected ether fractions were dried with $Na_2SO_4$. Then the dry, clear solution was acidified with ethanol saturated with HCl. The product crystallized out.

After several hours, it was filtered, washed and dried. The crude dihydrochloride of 1-(cyclopropylphenyl)-methyl-4-cinnamyl piperazine (melting point 272°–276°C) was obtained with a yield of 71%.

EXAMPLE 3

20.2 g (0.1 mole) of 1-cinnamyl piperazine (M.P 44°–46°C), 14 g of anhydrous $K_2CO_3$ and 20.3 g (0.1 mole) of (2-pyridyl phenyl)-methyl chloride (M.P 55°–57°C), freshly liberated from the hydrochloride of (2-pyridyl phenyl)-methyl chloride (M.P. 109°–110°C) in 100 ml of $N_1N$-dimethylformamide were heated between 40° and 50°C for 8 hours. After cooling, the mineral salts were filtered and the mother liquors were vacuum-evaporated below 50°C. The residue, 40 g, was crystalline. On recrystallising the crude product in 220 ml of benzene, 23.6 g of 1-(2'-pyridyl phenyl)-methyl-4-cinnamyl piperazine melting at 120°–122°C were obtained. The yield was 64%.

According to the processes described above in examples 1-3, the following products can be obtained:

1. 1-(4'-pyridyl-phenyl)-methyl-4-cinnamyl piperazine. M.P.: 118°–119°C.
2. 1-(3'-pyridyl-phenyl)-methyl-4-cinnamyl piperazine. M.P. 94°–99°C.
3. 1-(2',2''-dipyridyl)-methyl-4-cinnamyl piperazine. M.P. 122°–129°C.
4. 1-(2'-pyridyl-4''-chloro-phenyl)-methyl-4-cinnamyl piperazine. M.P. 105°–108°C.
5. 1-(cyclopentyl-phenyl)-methyl-4-cinnamyl piperazine. M.P. 198°–203°C.
6. 1-(cyclohexyl-phenyl)-methyl-4-cinnamoyl piperazine HCl. M.P. 208°–210°C.

EXAMPLE 4

11.9 g (.35 mmoles) of 2,2-dipyridyl methyl tosylate (M.P. 107°–110°C), 14.2 g of 1-cinnamyl piperazine in 50 ml anisole were refluxed for 5 hours. After filtering the 1-cinnamyl piperazine tosylate, the mother liquors were treated with active charcoal, filtered and the solvent distilled at reduced pressure. The solid residue (19.7 g) was recrystallized twice in 250 ml of isopropyl ether to obtain 8.15 g of 1-(2',2''-dipyridyl)-methyl-4-cinnamyl piperazine, having a melting point of 128°–129°C, corresponding to a yield of 62%.

EXAMPLE 5

To a solution of 11.6 g (0.065 mole) of N-bromosuccinimide and 0.2 g of benzoyl peroxide in 100 ml of carbon tetrachloride, 10 g (0.05 mole) of 2-(4-chlorobenzyl)-pyridine were introduced dropwise. After refluxing this mixture for 2 hours, at ambient temperature the succinimide formed was filtered, and the mother liquors evaporated. The brownish oily residue obtained (11.7 g) corresponds to α-(2-pyridyl)-4-chloro benzyl bromide, which was heating without any purification with 10.1 g of 1-cinnamyl piperazine and 12.0 g of anhydrous $Na_2CO_3$ in 80 ml of dry xylene for 4 hours. After cooling, the mineral salts were filtered, the solvent distilled and the semi-oily semi-cyrstalline residue was recrystallized in 250 ml of 60/90 benzine, to obtain 15.6 g of 1-(2'-pyridyl-4''-chlorophenyl)-methyl-4-cinnamyl piperazine melting at 105°–107°C. The yield was 71%, calculated on the basis of the 2-(4-chlorobenzyl)pyridine.

According to the processes described above in examples 1–5, the following products can be obtained:

1. 1-(cyclopentyl-phenyl)-methyl-4-cinnamyl piperazine dihydrochloride. M.P. 198°–203°C.
2. 1-(cyclohexyl-phenyl)-methyl-4-cinnamyl piperazine dihydrochloride. M.P. 239°–241°C.
3. 1(4'-pyridyl-phenyl)-methyl-4-cinnamyl piperazine. M.P. 118°–119°C.
4. 1-(3'-pyridyl-phenyl)-methyl-4-cinnamyl piperazine. M.P. 94°–96°C.
5. 1(2'-pyridyl-4''-fluorophenyl)-methyl-4-cinnamyl piperazine. M.P. 92°–94°C.
6. 1-(2'-pyridyl-2'',4''-dichlorophenyl)-methyl-4-cinnamyl piperazine trihydrochloride. M.P. 123°–127°C. (dec.)
7. 1-(2'-pyridyl-4''-chlorophenyl)-methyl-4-(4'λ chloro)-cinnamyl piperazine trihydrochloride. M.P. 186°–190°C.
8. 1-(2'-pyridyl-4''-chlorophenyl)-methyl-4-(4'-methyl)- cinnamyl piperazine.

9. 1-(2'-pyridyl-phenyl)-methyl-4-(3',4'-dioxymethylene)-cinnamyl piperazine. M.P. 76°–78°C.

10. 1-(2'-pyridyl-4''-chlorophenyl)-methyl-4-(3',4',5'-trimethoxy)-cinnamyl piperazine.

EXAMPLE 6

A flask containing a solution of 21.6 g (0.1 mole) of 1-(cyclopropyl phenyl)-methyl piperazine (boiling point: 147°–148°C), at a pressure of 1.8 to 2 mm of Hg in 100 ml of dry benzene was cooled to 5°C. 11 g of anhydrous $Na_2CO_3$ were added, and a solution of 16.6 g (0.1 mole) of cinnamoyl chloride in 50 ml of dry benzene was introduced dropwise, with stirring; this addition was effected at a rate such that the temperature of the mixture did not rise above 10°C. It was then left to return to the ambient temperature, it was stirred for another 12 hours, and the mixture was brought to a temperature between 40° and 50°C for 4 hours. It was then cooled, the mineral salts were filtered and the mother liquors were acidified with hydrochloric acid dissolved in isopropanol. 24.5 g of crude 1-(cyclopropyl phenyl)-methyl-4-cinnamoyl piperazine hydrochloride were thus obtained, having a melting point of 220°–222°C, and which can be recrystallized if desired.

The yield was 90.1%.

According to the method described in example 6, the following product can be obtained:

1-(cyclohexyl-phenyl)-methyl-4-cinnamoyl piperazine hydrochloride. M.P. 208°–210°C.

EXAMPLE 7

20.5 g (64 mmoles) of 3-(2-pyridyl-4'-chloro phenyl)-propionaldehyde diethyl acetal in 150 ml of 10% $H_2SO_4$ were heated with stirring at 90°–95°C for 30 minutes under a nitrogen atmosphere. This was cooled to 15°C, diluted with 100 ml of benzene, neutralized (pH = 7) with a 30% solution of NaOH, then the two phases were separated, the aqueous phase was washed with benzene, the collected benzene phases were dried over $MgSO_4$, they were filtered and vacuum-concentrated. The crude aldehyde (14.5 g) was obtained with a yield of 92%. The mixture of 14.5 g of this crude aldehyde, 9.5 g of 1-cinnamyl piperazine and 2.5 ml of formic acid were heated for 1 hour at 100°C, then at 125°–135°C for 16 hours. Finally, at about 50°C, the mixture was dissolved in 150 ml of chloroform, the chloroform solution was extracted with three × 100 ml of 10% HCl, the aqueous layer was treated with active charcoal, filtered, alkalinised with a 30% solution of NaOH and extracted with chloroform. The chloroform phase was dried and the vacuum evaporated. The viscous orange residue weighs 13.8 g, that is 68% of the theoretical calculated on the basis of 1-cinnamyl piperazine. By dissolving this crude base in 100 ml of absolute ethanol and treating with a boiling solution of 4.7 g of fumaric acid in 100 ml of absolute ethanol, 15 g of 1-[3-(2-pyridyl-4'-chlorophenyl]-propyl-4-cinnamyl piperazine fumarate were obtained. M.P. 224°–228°C.

According to the method described above in example 7, 1-[3-(2-pyridyl-phenyl]-propyl-4-cinnamyl piperazine fumerate, M.P. 220°–225°C, and 1-[3-(4'-chlorophenyl)3-(2''-pyridyl)-3-hydroxy]-propyl-4-cinnamyl piperazine, M.P. 77°–79°C can be obtained.

EXAMPLE 8

To a suspension of 50 mmoles of n-butyl lithium in 150 ml of dry ether under a nitrogen atmosphere, the solution of 8 g (50 mmoles) of 2-bromo pyridine in 5 ml of dry ether were added at −18°C, and after 30 minutes, still at −18°C the solution of 8.35 g (25 mmoles) of 3-(4'-cinnamyl)-piperazyl-(1')-propiophenone (M.P. 75°–77°C) in 50 ml of dry tetrahydrofuran was introduced. This was stirred overnight at ambient temperature, the complex was decomposed with 100 ml of water, the two phases were separated, the aqueous phase washed with ether, dried over $Na_2SO_4$ and vacuum-evaporated. On recrystallizing the oil obtained (13.6 g) in 130 ml of isopropyl ether, 7.6 g of 1-[3-phenyl-3-(2'-pyridyl)-3-hydroxy]-propyl-4-cinnamyl piperazine crystallized out.

Melting point: 110°–112°C.

The yield was 74%.

According to the method described above in example 8, 1-[3-(4'-chlorophenyl)-3-(2''pyridyl)-3-hydroxy]-propyl-4-cinnamyl piperazine, M.P. 77°–79°C, can be obtained.

EXAMPLE 9

A solution of 6.9 g of 1-[3-(4'-chlorophenyl)-3-(2''-pyridyl)-3-chloro]-propyl-4-cinnamyl piperazine trihydrochloride (M.P. 103°–105°C) (12 mmoles) in 50 ml of dry pyridine was heated for 3 hours at 80°C, and then refluxed for 2 hours. Then the solvent was vacuum-distilled and the tarry residue (10.3 g) was taken up in 100 ml of N HCl, refluxed, treated with active charcoal, filtered, to the clear yellowish solution at ambient temperature was added a solution of 3 g of maleic acid in 10 ml of $H_2O$. After a few hours the 1-[3-(4'-chlorophenyl)-3-(2''-pyridyl)]-2-propenyl-4-cinnamyl piperazine dimaleate melting at 182°–183°C crystallized out.

EXAMPLE 10

To a solution of 9.7 g (24 mmoles) of 1-(2'-pyridyl-4''-chlorophenyl)-methyl-4-cinnamyl piperazine in 100 ml of dry tetrahydrofuran under a nitrogen atmosphere, were added dropwise over 30 minutes 62 ml of an ether solution containing 27 mmoles of phenyl lithium. While stirring for 30 minutes at room temperature 3.7 g (27 mmoles) of butyl bromide dissolved in 50 ml of dry ether were added. This was left, with stirring, at room temperature for 48 hours, and then cooled to 0°C, hydrolyzed with 100 ml of $H_2O$, the phases separated, the aqueous phase was washed with ether and the collected ether phases dried over $MgSO_4$, and the vacuum-concentrated. 9.5 g of oily product were obtained, which were dissolved in 20 ml of ethanol treated with a boiling solution of 3.4 g of fumaric acid in 50 ml of ethanol. After adding 70 ml of isopropylether to this solution, the 1-(2'-pyridyl-4''-chloro-phenyl-n-butyl)-methyl-4-cinnamyl piperazine crystallized out. After several hours these crystals were filtered (11.0 g) which have a melting point of 178°–181°C; the yield was 79%.

According to the method described above in example 10, 1-(2'-pyridyl-4''-chloro phenyl methyl)-methyl-4-cinnamyl piperazine fumarate can be obtained. M.P. 186°–187°C.

EXAMPLE 11

The sodium salt of 17.6 g (0.08 mole) of 2-pyridyl-4-chlorophenyl methanol in 200 ml of dry xylene was prepared with a 50% oil dispersion of NaH, by refluxing for 6 hours. 225 ml of an isopropylether solution containing 22 g of 1-β-chloroethyl-4-cinnamyl piperazine, then, after evaporating the isopropylether, the mixture was refluxed for 15 hours. After cooling the mineral salts were filtered, the mother liquors extracted three times with 100 ml of N HCl, the aqueous solution was treated with active charcoal, alkalinised with concentrated $NH_4OH$, the base extracted with chloroform, and evaporated. The residue obtained (16.3 g) was crystallized in 200 ml of isopropylether to give the (2-pyridyl-4-chlorophenyl)-methyl-$\beta$-(4-cinnamyl piperazyl)-ethyl ether having a melting point of 68°–72°C. Tests relating to the products having the following substituants:

R = Ph, $R_1$ = 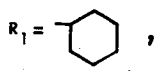, $R_2$ = H, Q = O, X = >CO, $R_3$ = H
and
R = Ph, $R_1$ = 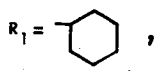, $R_2$ = H, Q = O, X = >$CH_2$, $R_3$ = H.

Acute toxicity

Tests were performed on mice, orally (P.O.) and intraperitoneally (I.P.), the active compounds being suspended in gum syrup or labrafil.

TABLE I

| X | | LD 50 (mg/kg) | LD 0 |
|---|---|---|---|
| C = O | P.O. | > 4000 | > 1000 |
|  | I.P. | 1480 | > 400 |
| —$CH_2$— | P.O. | 570 | ≅ 300 |

In particular, 1-(cyclo propyl phenyl)-methyl-4-cinnamoyl piperazine appears to have a very low toxicity. Moreover, because of the volume of substance to be administered, the dose of 4000 mg/kg for products in suspension is not exceeded.

Tests relating to the trihydrochloride of the product having the following substituants:
R = Ph, $R_1$ = 2-pyridyl, $R_2$ = H,
Q = O, X = >$CH_2$, $R_3$ = H.

Acute toxicity

Tests were performed on mice and albino rats, the active compound being administered orally in the form of an aqueous solution.

TABLE II

| | $LD_0$ mg/kg | $LD_{50}$ mg/kg |
|---|---|---|
| mice | 175 | 295 |
| rats | 200 | 1200 |

Tests relating to the products having the following substituants:
a. R=4—Cl—$C_6H_4$—, $R_1$=2-pyridyle, $R_2$=H, Q=O, X=>$CH_2$, $R_3$=H.
b. R = Ph, $R_1$ = 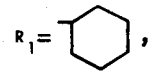 , $R_2$=H, Q=O, X=>$CH_2$, $R_3$=H.
c. R=4—F—$C_6H_4$—, $R_1$=2-pyridyle, $R_2$=H, Q=O, X=>$CH_2$, $R_3$=H.
d. R=2,4—$Cl_2C_6H_3$—, $R_1$=2-pyridyle, $R_2$=H, Q=O, X=>$CH_2$, $R_3$=H.
e. R=4—Cl—$C_6H_4$—, $R_1$=2-pyridyle, $R_2$=$CH_3$, Q=O, X=>$CH_2$, $R_3$=H.

The products were used in the form of the trihydrochloride, except the product under the letter "b" which was used in the form of the dihydrochloride.

TABLE III

| Products | Toxicity (mice) I.G. | |
|---|---|---|
| | $LD_0$ mg/kg | $LD_{50}$ mg/kg |
| R = 4-Cl—$C_6H_4$—<br>$R_1$ = 2-pyridyl<br>$R_2$ = H | 400 | 1180 |

TABLE III -continued

| Products | Toxicity (mice) I.G. | |
|---|---|---|
| | $LD_0$ mg/kg | $LD_{50}$ mg/kg |
| R = Ph,<br>$R_1$= 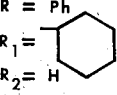<br>$R_2$= H | 100 | 600 |
| R = 4-F—$C_6H_4$—<br>$R_1$ = 2-pyridyl<br>$R_2$ = H | 300 | 400 |
| R = 2,4-$Cl_2C_6H_3$—<br>$R_1$ = 2-pyridyl<br>$R_2$ = H | 400 | 600 |
| R = 4-Cl—$C_6H_4$—<br>$R_1$ = 2-pyridyl<br>$R_2$ = $CH_3$ | 400 | 500 |

The set of methods and tests effected enabled us to appreciate the activity of the products according to the invention. It clearly follows therefrom that the products wherein:

R = 4—Cl—$C_6H_4$—, $R_1$ = 2-pyridyl, $R_2$= H; R = 2,4—$Cl_2$—$C_6H_3$-,
$R_1$= 2-pyridyl, $R_2$ = H, and R = 4F—$C_6H_4$—, $R_1$ = 2-pyridyl,
$R_2$ = H, present well-defined vasodilatatory spasmolytic and antihistaminic activities. They do not show depressant and neurotoxic properties.

The product wherein R = Ph, $R_1$= 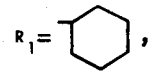 , $R_2$ = H, shows a well-marked cholinolytic activity.
It also does not show depressant and neurotoxic properties.

The product wherein R = 4—Cl—$C_6H_4$, $R_1$ = 2-pyridyl, $R_2$ = $CH_3$ presents a sedative activity.

The product wherein R = 4—Cl—$C_6H_4$—, $R_1$ = 2-pyridyl, and $R_2$ = H also presents an important activity with respect to cerebral circulation.

In the course of a series of experiments on cats anaesthetized with Nembutal, the cynetics of $PO_2$ of the venous cerebral blood were measured (from the sinus sagittalis) during an intravenous perfusion of this product.

For all these products the daily does is approximately 5 mg to 500 mg, according to the mode of application, and the toxicity.

We claim:
1. A compound of the formula

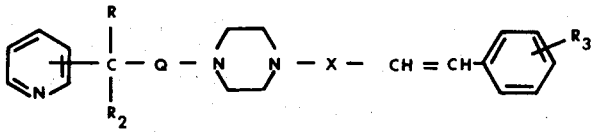

wherein X represents a carbonyl group >C=O or a methylene group —$CH_2$—,

R represents a phenyl, mono- or di-halophenyl or 2-pyridyl group, $R_2$ represents hydrogen, hydroxy or a $C_{1-5}$-alkyl group, $R_3$ represents 1 to 3 groups which can be hydrogen, halogen, $C_{1-3}$-alkyl, methoxy or dioxymethylene, and Q represents the $(CH_2)_n$ group, $n$ having the value 0, 1, 2, 3, the —CH=CH—CH$_2$— or —O—CH$_2$—CH$_2$— group.

2. A compound of the formula

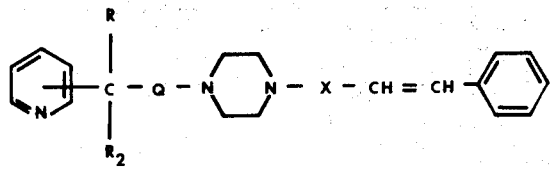

wherein X represents a carbonyl group >C=O or a methylene group —CH$_2$—,
R represents a phenyl, mono- or di-halophenyl or 2-pyridyl group,
R$_2$ represents hydrogen, hydroxy or a C$_{1-5}$-alkyl group, and
Q represents the $(CH_2)_n$ group, n having the value 0, 1, 2, 3, the —CH=CH—CH$_2$— or —O—CH$_2$—CH$_2$— group.

* * * * *